United States Patent
Schneider et al.

(10) Patent No.: US 7,384,899 B2
(45) Date of Patent: Jun. 10, 2008

(54) ANIMAL SHAMPOO

(75) Inventors: David J. Schneider, Union, KY (US); Charles A. Schneider, Villa Hills, KY (US)

(73) Assignee: Schneider Advanced Technologies, Inc., Covington, KY (US)

( * ) Notice: Subject to any disclaimer, the term of this patent is extended or adjusted under 35 U.S.C. 154(b) by 0 days.

(21) Appl. No.: 11/243,813

(22) Filed: Oct. 5, 2005

(65) Prior Publication Data

US 2006/0073995 A1 Apr. 6, 2006

Related U.S. Application Data

(60) Provisional application No. 60/616,597, filed on Oct. 6, 2004.

(51) Int. Cl.
*C11D 3/32* (2006.01)
*C11D 7/12* (2006.01)

(52) U.S. Cl. ............ 510/160; 510/131; 510/382; 510/386; 510/501; 510/509

(58) Field of Classification Search ............ 510/160, 510/131, 382, 386, 501, 509
See application file for complete search history.

(56) References Cited

U.S. PATENT DOCUMENTS

| 3,754,878 | A | * | 8/1973 | Burke | 51/307 |
| 3,980,673 | A | * | 9/1976 | Siegle et al. | 549/470 |
| 4,146,496 | A | * | 3/1979 | Gray | 8/111 |
| 4,309,425 | A | * | 1/1982 | Cheng | 514/183 |
| 5,205,955 | A | * | 4/1993 | Bunczk et al. | 510/192 |
| 5,702,690 | A | * | 12/1997 | Dubief et al. | 424/70.1 |
| 6,383,996 | B1 | * | 5/2002 | Maurin et al. | 510/119 |
| 2003/0165546 | A1 | * | 9/2003 | Resch et al. | 424/401 |
| 2004/0063796 | A1 | * | 4/2004 | Winston et al. | 516/79 |
| 2004/0225017 | A1 | * | 11/2004 | Schneider | 514/612 |
| 2006/0057075 | A1 | * | 3/2006 | Arkin et al. | 424/47 |

* cited by examiner

*Primary Examiner*—Charles I Boyer
(74) *Attorney, Agent, or Firm*—Richard M. Klein; Fay Sharpe LLP

(57) ABSTRACT

This invention is concerned with odor control animal shampoo. Odor control animal shampoos in accordance with this invention comprises a shampoo base to which is added a halo sulfonamide compound. In use the halo sulfonamide compound, as is contained in the shampoo, reacts with odorous nitrogen and sulfur bearing compounds which are contained on the body of a pet. The halo sulfonamide compound reacts with the nitrogen and sulfur compounds to reduce these compounds to a non odorous format. The animal shampoo of this invention are particularly effective in controlling odors which originate on dogs and cats. The halo sulfonamide compound can be present in the shampoo formulation at any effective concentrations. Shampoo formulations which incorporate from about 0.1 to about 5.0 weight percent of a halo sulfonamide compound have been found to be effective. Chloramine-T is a preferred sulfonamide compound for use as an odor control agent in the shampoo formulations of this invention.

15 Claims, No Drawings

ANIMAL SHAMPOO

RELATED APPLICATIONS

This application claims priority of Provisional Application Ser. No. 60/616,597 filed Oct. 6, 2004

BACKGROUND OF THE INVENTION

This invention is concerned with the control and removal of various odors, which are associated with animals. An important embodiment of this invention is the control of animal body odors. In particular this invention is concerned with animal shampoo.

In its broadest sense this invention relates to an animal shampoo which functions as an odor control agent, for controlling odors which are associated with pets. In the prior art animal odor control was effected by treating the animal with a perfume. This prior art method for odor control only mask the various complex odor causing molecules. In contrast in this invention these molecules are reacted with a halgonated sulfonamide compound in such a manner that the odorous molecules are destroyed, or altered to a non-odorous format. This conversion is effected when the shampoo of this invention is used.

1. Prior Art

Pet odor control in the prior art has been effected by treating the pet with a perfume. This perfume mask the troublesome odors but does not alter the odor causing agents on a molecular level. In this invention the odor causing molecules are caused to react with a halgonated sulfonamide compound on a molecular level. The reaction in question converts the odorous substances into substances which are non-odorous. In accordance with this invention odor control is effected by washing the animal with the defined shampoo.

2. Objects of the Invention

An object of this invention is an effective way to control odors which are emitted by pets, by utilization of a shampoo which contains a sulfonamide compound.

Another object of this invention is an improved animal shampoo.

Still another object of this invention is an improved animal shampoo which has residual odor control properties.

DESCRIPTION OF THE PREFERRED EMBODIMENT

Dogs and cats were domesticated by man and kept as pets thousands of years ago. Evidence that cats were domesticated has been found in ancient Egyptian tombs.

When cats are kept as pets in close proximity to humans the problem always comes up as to how to minimize the animals body odors. In years past the answer was simple, that is, give the animal a bath using a household soap product. While this procedure worked to a degree the general concept left much to be desired. While this prior art method for pet odor control was useful the pet odors were only mitigated for a short period of time.

In recent years as society became more affluent specific shampoos for animals were developed and have been put into usage.

The subject animal shampoo is useful in conjunction with any animal and in particular cats and dogs.

The use of the subject shampoo makes pets and in particular cats and dogs more pleasant to be around.

The problem with the prior art pet shampoos is that, while they temporarily mitigated the pet odors, the odors were not attacked on a molecular level and hence the odors soon returned.

Pet odors essentially result from odorous nitrogen and sulfur bearing compounds which are secreted by the pet.

In accordance with this invention the animal shampoo incorporates a N-halogenated sulfonamide aromatic compound or compounds which will react with the troublesome odor causing nitrogen and sulfur bearing compounds which cause pet odors.

Most animal shampoos are nothing more than perfumed liquid soap. In this invention an N-halogenated sulfonamide aromatic compound is incorporated into the animal shampoo in such a manner that it can react with the odorous nitrogen and sulfur bearing compounds which cause animal body odor.

While any suitable halogenated compound may be utilized as an active reactant for use in animal shampoo, Chloramine-T has been found to be particularly useful.

The animal shampoo of this invention incorporates an N-halogenated sulfonamide aromatic compound which is formulated into the shampoo base. The concentration of the N-halogenated sulfonamide aromatic compound, in the shampoo formulation may vary with the particular N-halogenated sulfonamide aromatic compound utilized.

Regardless of the shampoo formulation, in a broad sense the concentration of the N-halogenated sulfonamide aromatic compound, in the shampoo, can be from 0.01 to about 10 weight percent based on the weight of the shampoo substrate. Another range is from about 0.1 to about 1.5 weight percent with still another range being from about 0.2 to about 0.1 weight percent. A useful percentage is 0.5 weight percent.

The pet shampoo of this invention may further incorporate a buffering agent such as sodium bicarbonate.

When treated with the N-halogenated sulfonamide aromatic compound the shampoo may have detectable bleach odor. In order to mask this bleach odor the shampoo may further incorporate trace amounts of a perfume. Likewise the shampoo may further be dyed to any desired color.

A shampoo is essentially a solution of a surface active agent (surfactant) to which additives have been added. The additives can be incorporated into the solution for a variety of purposes. For example if the additives is an insecticide the surfactant solution can be a flea shampoo for use on pets. If a biocide is added to the surfactant solution the resulting shampoo can have medical properties for the cure of maladies such as dandruff and mange. Further the shampoo can include colorant additives whereby the color of hair can be altered for example the color graying hair. Shampoos with colorant additives are usually for human use.

In accordance with the subject invention an odor control additive is added to a shampoo base. This invention is concerned with the use of a sulfonamide additive to control pet odors. In this invention the surfactant component of the shampoo allows the shampoo solution to thoroughly wet out the skin and fur of the animal. The active component of the shampoos of this invention is a specific sulfonamide compound. Once the skin and fur of the pet is wetted out the sulfonamide compound is carried into the animal fur and onto the skin of the animal. If secreted odorous nitrogen and sulfur bearing compounds are present on the animal these compounds are altered by their contact with the sulfonamide compound as is contained in the shampoo. In other words the sulfonamide component of the shampoo reacts with the odorous nitrogen and sulfur compounds in such a manner that they are reduced to a non odorous format. This reaction effectively deodorizes the pet in question. The surfactant enhances the ability of sulfonamide component to come into contact with the odorous secretions.

Suitable bases for formulating the shampoo of this invention are aqueous solutions of nonionic, cationic and anionic wetting agents. Using these bases pet shampoos are formulated in accordance with the discussion herein.

Suitable halogenated sulfonamide compounds which may be used to formulate pet shampoos in accordance with this invention, are represented by the following formula.

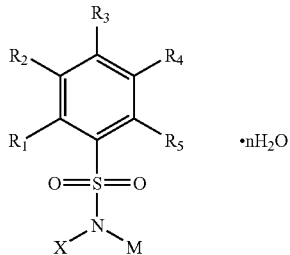

Wherein;

X is a halogen

R1, R2, R3, R4, R5 are hydrogen, COOH, derivatized COOH, an ester or alkylated amide, COOM, CN, $NO_2$, $SO_2H$ or derivatized $SO_3R$, a halogen, a substituted or unsubstituted phenyl group, a sulfonamide, a halosulfonamide, a straight or branched aliphatic moiety from C1 to C12 wherein, the same straight or branched aliphatic moiety may contain substitution at one ore of the aliphatic hydrogens and M is an alkali or alkaline earth metal.

A preferred sulfonamide compound for use in the pet shampoos of this invention is Chloramine-T.

As to the above set forth compounds it should be noted that the location of the substitution on the aromatic ring can have an affect on the stability and activity of the compound as an odor control agent and stability in shampoo formulation.

For use in this invention aqueous solutions of N-halogenated sulfonamide compounds are preferred however, shampoos which are based on solvents other than water may also be used.

The pH of the odor control shampoo with this invention should be above 7.

The following examples will illustrate odor control in an animal litter environment in accordance with the subject invention. The examples in particular demonstrate pet odor control. These examples are given for purposes of illustration and not for purposes of limiting this invention.

EXAMPLE 1

A shampoo having the following formulation was prepared:
25 g (10%) Sodium Laureth Sulfate
13 g (5.2%) Sodium Lauryl Sulfate
5 g (2%) Cocamidopropyl betaine
2.4 g (1%) N-chloro-4-carboxybenzenesulfonamide disodium salt
204.6 g (81.8%) water
Sodium bicarbonate was added to adjust pH just below 9
Solution was stirred and stability studies were performed at room temperature
After 49 days, 84.8% of the N-chloro-4-carboxybenzenesulfonamide disodium
Salt
Active ingredient remained
The formulation exhibited odor control properties.

EXAMPLE 2

On another shampoo having the following formulation was prepared:
62 g (24.8% Sodium Lauryl Sulfate
2.4 g (1%) N-chloro-4-carboxybenzenesulfonamide disodium salt
185.6 g (74.2%) water
Sodium bicarbonate was added to adjust pH to 9
Solution was stirred and stability studies were performed at room temperature
After 62 days 100% of the N-chloro-4-carboxybenzenesulfonamide disodium salt
Active ingredient remained
The formulation exhibited odor control properties.

EXAMPLE 3

Still another shampoo having the following formulation was prepared:
20.7 g (8.3%) Sodium lauryth sulfate
20.7 g (8.3%) Sodium C14-C16 olefin sulfonate
20.7 g (8.3%) Sodium alkyl glycidyl ether sulfonate
2.4 g (1%) N-chloro-4-carboxybenzenesulfonamide disodium salt
185.6 g (74.2%) water
Sodium bicarbonate was added to adjust pH to 9
Solution was stirred and stability studies were performed at room temperature
After 62 days, 88.1% of the N-chloro-4-carboxybenzenesulfonamide disodium
Salt
Active ingredient remained.
Again the shampoo exhibited odor control properties.

What is claimed is:

1. An odor control animal shampoo which comprises a liquid shampoo base which incorporates an effective amount of an N-halogenated, sulfonamide aromatic compound, an effective amount of an insecticide, and an amount of sodium bicarbonate effective to adjust the pH of the shampoo to about 9;

wherein the N-halogenated, sulfonamide aromatic compound has the following formula:

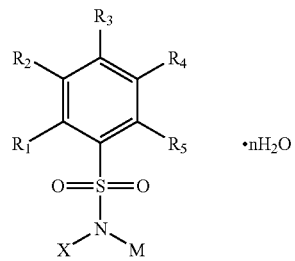

wherein X is a halogen;
$R_1$, $R_2$, $R_3$, $R_4$, $R_5$, are hydrogen, COOH, derivatized COOH, an ester or alkylated amide, COOM, CN, $NO_2$, $SO_3H$ or derivatized $SO_3R$, a halogen, substituted or unsubstituted phenyl group, a sulfonamide, a halosulfonamide, a straight or branched aliphatic moiety from $C_1$-$C_{12}$ which may be substituted at one or more of the aliphatic hydrogens; and M is an alkali or alkaline earth metal.

2. The animal shampoo of claim 1 wherein the shampoo base is a member selected from the group consisting of solutions of anionic, cationic and non ionic wetting agents.

3. The animal shampoo of claim 1, wherein the shampoo base is a solution of an anionic wetting agent.

4. The animal shampoo of claim 1 wherein the N-halogenated, sulfonamide compound is Chloramine-T.

5. The animal shampoo of claim 1 wherein the shampoo base contains from about 0.01 to about 5.0 weight percent of the N-halogenated, sulfonamide aromatic compound.

6. The animal shampoo of claim 2 wherein the shampoo base contains from about 0.01 to about 5.0 weight percent of the N-halogenated, sulfonamide aromatic compound.

7. The animal shampoo of claim 3 wherein the shampoo base contains from about 0.01 to about 5.0 weight percent of the N-halogenated, sulfonamide aromatic compound.

8. The animal shampoo of claim 4 wherein the shampoo base contains from about 0.01 to about 5.0 weight percent Chloramine T.

9. The animal shampoo of claim 5 wherein the shampoo base contains from about 0.1 to about 1.5 weight percent of the N-halogenated, sulfonamide aromatic compound.

10. The animal shampoo of claim 6 wherein the shampoo base contains from about 0.1 to about 1.5 weight percent of the N-halogenated, sulfonamide aromatic compound.

11. The animal shampoo of claim 7 wherein the shampoo base contains from about 0.1 to about 1.5 weight percent of the N-halogenated, sulfonamide aromatic compound.

12. The animal shampoo of claim 8 wherein the shampoo base contains from about 0.1 to about 1.5 weight percent of the N-halogenated, sulfonamide aromatic compound.

13. An animal shampoo comprising:
aqueous solution selected from the group consisting of solutions of anionic, cationic and non ionic wetting agents;
an amount of sodium bicarbonate sufficient to adjust the pH to about 9;
an effective amount of an insecticide; and
an effective amount of an N-halogenated, sulfonamide aromatic compound of the following formula:

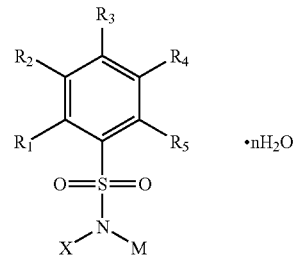

wherein X is a halogen;
$R_1$, $R_2$, $R_3$, $R_4$, and $R_5$ are independently hydrogen, COOH, derivatized COOH, an ester or alkylated amide, COOM, CN, $NO_2$, $SO_3H$ or derivatized $SO_3R$, a halogen, a substituted or unsubstituted phenyl group, a sulfonamide, a halosulfonamide, a straight or branched aliphatic moiety from C1-C12 which may be substituted at one or more of the aliphatic hydrogens; and M is an alkali or alkaline earth metal.

14. The shampoo of claim 13 wherein the shampoo contains from about 0.01 to about 5.0 weight percent of the N-halogenated, sulfonamide aromatic compound.

15. The shampoo of claim 13 wherein the N-halogenated, sulfonamide compound is Chloramine-T.

* * * * *